(12) United States Patent
Borts et al.

(10) Patent No.: US 7,115,413 B2
(45) Date of Patent: Oct. 3, 2006

(54) MEIOTIC RECOMBINATION IN VIVO OF PARTIALLY HOMOLOGOUS DNA SEQUENCES

(75) Inventors: Rhona Harriet Borts, Sutton nr Witney (GB); Edward John Louis, Sutton nr Witney (GB)

(73) Assignee: Mixis France S.A., Paris (FR)

( * ) Notice: Subject to any disclaimer, the term of this patent is extended or adjusted under 35 U.S.C. 154(b) by 0 days.

(21) Appl. No.: 09/155,452

(22) PCT Filed: Mar. 27, 1997

(86) PCT No.: PCT/GB97/00875

§ 371 (c)(1),
(2), (4) Date: Oct. 23, 1998

(87) PCT Pub. No.: WO97/37011

PCT Pub. Date: Oct. 9, 1997

(65) Prior Publication Data

US 2002/0013956 A1    Jan. 31, 2002

(51) Int. Cl.
*C12N 5/00* (2006.01)
*C12N 15/00* (2006.01)
*C12N 1/14* (2006.01)
*C07H 21/02* (2006.01)
*C07H 21/04* (2006.01)

(52) U.S. Cl. .................... 435/325; 536/23.1; 536/23.4; 435/320.1; 435/254.2

(58) Field of Classification Search ................. 800/21; 435/455
See application file for complete search history.

(56) References Cited

FOREIGN PATENT DOCUMENTS

WO        90 07576 A    7/1990

OTHER PUBLICATIONS

Thomas, "Advances in the genetics and molecular biology of colorectal tumors", Curr. Opin. Oncol., 6(4):406-412.*
Reitmair et al. 'MSH2 deficient mice . . . ' Nat Genet 11(1):64-70 (Sep. 1995).*
Edelmann et al. 'Meiotic Pachytene arest . . . ' Cell 85:1125-1134 (1996).*
Santucci-Darmanin et al. 'MSH4 acts in conjunction . . . ' FASEB J 14:1539-1547 (2000).*
Lipkin et al. 'Meiotic arrest and . . . ' Nature Genetics 31:385-390 (Aug. 2002).*
Moens et al. 'The time course and chromosomal . . . ' J cell Sci 115:1611-1622 (2002).*
E. Alani et al., "Interaction between mismatch repair and genetic recombination in saccharomyces cerevisiae", Genetics, vol. 137, No. 1, pp. 19-39, May 1994.
T.A. Prolla et al., "Dual requirement in yeast DNA mismatch repair for MLH1 and PMS1: two homologs of the bacterial mutl gene", Molecular and Cellular Biology, vol. 14, No. 1, pp. 407-415, Jan. 1994.
E.M. Selva et al., "Mismatch correction acts as a barrier to homologous recombination in saccharomyces cerevisiae", Genetics, vol. 139, No. 3, pp. 1175-1188, Mar. 1, 1995.
N. Hunter et al., "The mismatch repair system contributes to meiotic sterility in an interspecific yeast hybrid", Embo Journal, vol. 15, No. 7, pp. 1726-1733, Apr. 1, 1996.
S.R. Chambers et al., "The mismatch repair system reduces meiotic homologous recombination and stimulates recombination-dependent chromosome loss", Molecular and Cellular Biology, vol. 16, No. 11, pp. 6110-6120, Nov. 1996.

* cited by examiner

*Primary Examiner*—Joseph Woitach
(74) *Attorney, Agent, or Firm*—Rader, Fishman & Grauer PLLC

(57) ABSTRACT

Process for the meiotic recombination in vivo of partially homologous DNA sequences having up to 30% of base mis-matches, wherein eukaryotic cells containing the sequences and in which an enzymatic mismatch repair system is defective, are maintained under conditions to effect meiosis. Preferably the enzymatic mismatch repair systems of the eukaryotic cells are defective by virtue of at least one mutS protein and/or at least one mutL protein being defective or missing. The eukaryotic cells may be unicellular organisms such as yeasts.

5 Claims, 1 Drawing Sheet

MEIOTIC RECOMBINATION IN VIVO OF PARTIALLY HOMOLOGOUS DNA SEQUENCES

BACKGROUND OF INVENTION

1. Field of the Invention

This invention is related to the field of meiotic recombination of partially homologous DNA sequences.

2. Description of the Related Art

Genetic recombination is dependent on the formation of a near perfectly paired heteroduplex joint molecule containing complementary strands from two homologous DNA duplexes. Reduced homology between substrate molecules decreases the efficiency of recombination. A striking example of this can be seen during interspecific crosses between *Escherichia coli* and *Salmonella typhymurium*. The genomes of these two bacterial species are diverged by approximately 16%. At this level of heterology the frequency of recombination during conjugational crosses is reduced by up to 5 orders of magnitude. The barrier to recombination is largely dependent on the activity of the mismatch repair system The "disrupted species barrier" and "chromosomal instability" phenotypes, seen in bacterial mismatch repair mutants, are thought to result from a failure to prevent interactions between homeologous (closely related but non-identical) DNA sequences. This process has been termed antirecombination, although its molecular basis remains unclear. The existence of this activity has led to the proposal that the mismatch repair system is involved in controlling the fidelity of genetic exchanges. By only permitting crossovers between truly homologous sequences, such a process would suppress ectopic interactions between dispersed homologous sequences and thereby avoid potentially lethal chromosome rearrangements. Hence, the recognition of mismatches in duplex DNA may play a role in maintaining the structural integrity of chromosomes.

Many of the elements of the long-patch mismatch repair system that are believed to be involved in antirecombination have been organism of which the enzymatic mismatch repair system is defective or has been inactivated transitorily, particularly by saturation, for a time to obtain recombination between the DNA sequences. Although the specification envisages the possibility of performing such recombinations in bacteria, yeasts, plant or animal cells, in fact the experimental data provided only demonstrate such recombinations in bacteria of different genera, where the recombinations are achieved by a process of mitotic recombination.

In eukaryotes, the enzymatic mismatch repair systems are more complex than in prokaryotes. Also, the enzymatic mismatch repair systems involved in meiosis are to some extent different from those involved in mitosis. It was therefore not predictable that the technique generally described in the aforesaid European patent specification could be successfully applied to eukaryotic cells undergoing meiosis.

SUMMARY OF THE INVENTION

The present invention provides process for the meiotic recombination in vivo of partially homologous DNA sequences having up to 30% of base mismatches, wherein eukaryotic cells containing the sequences and in which an enzymatic mismatch repair system is defective, are maintained under conditions to effect meiosis. Preferably hybrid genes and their coded proteins are formed by the process.

Figure 1:
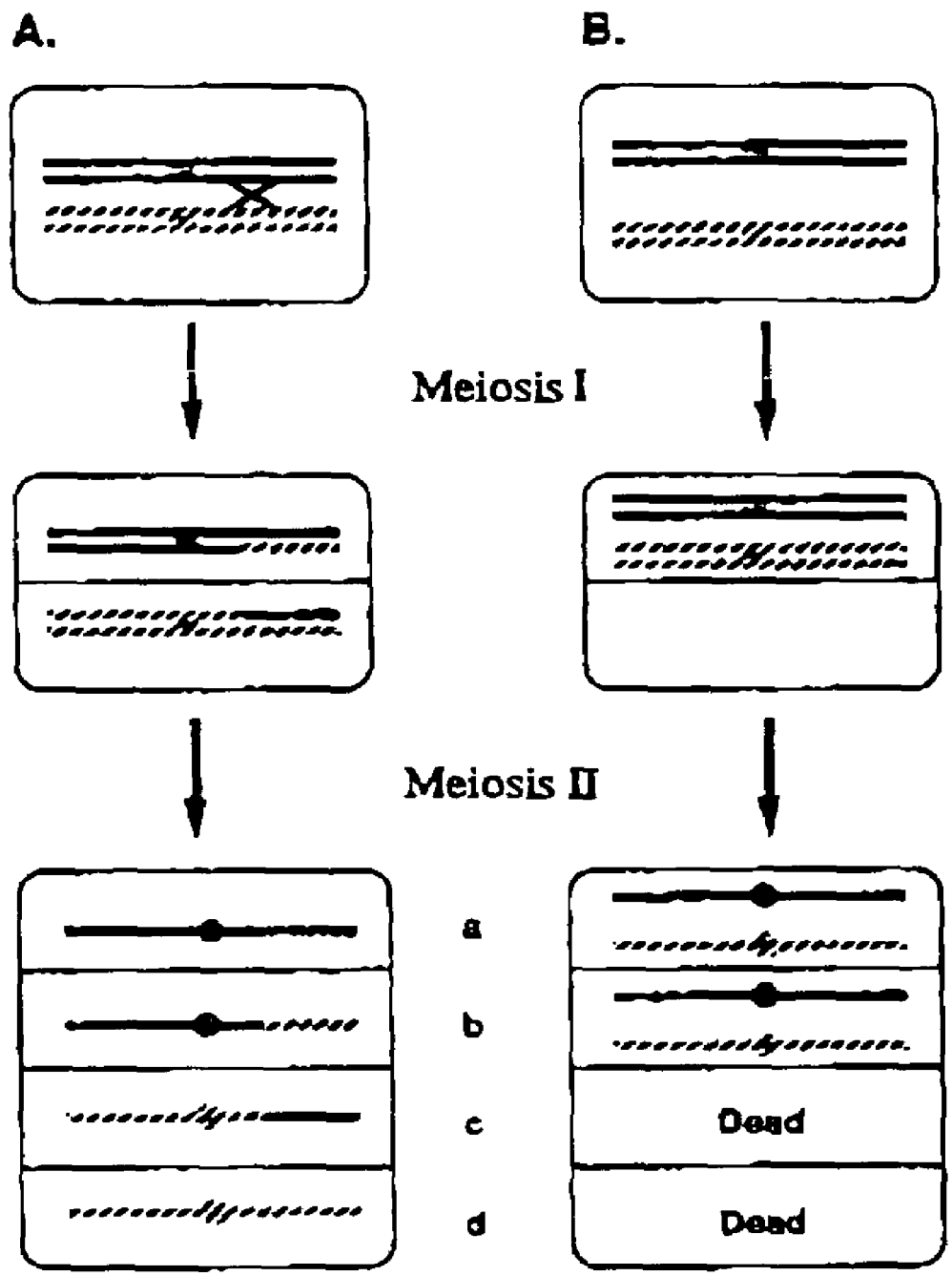
FIG. 1. A model of the biological consequences of antirecombination during meiosis A. Homologous chromosomes recombine and undergo crossing over. The homologous become physically connected by a chiasmata and consequently orientate correctly on the meiosis I spindle. Correct disjunction in the first division is followed by an equational division to produce four euploid spores. Spores b. and c. contain recombinant chromosomes.

B. The mismatch repair protein will prevent a crossover between homologous chromosomes. Apposition of the centrosomes is not ensured and the resultant univalents segregate randomly with respect to each other at meiosis I. If both univalents attach at the same spindle nondisjunction will result. After meiosis, two disomic and two nullosomic spores will be produced. None of the chromosomes will be recombinant. The nullosomic cells lack essential genetic information and will be dead. The disomic cells contain unbalanced genomes and may have reduced fitness.

DESCRIPTION OF THE PREFERRED EMBODIMENTS

Preferably the process is performed for making hybrid eukaryotic species by providing a set of first eukaryote cells containing a first DNA sequence and in which an enzymatic mismatch repair system is defective; providing a set of second eukaryotic cells containing a second DNA sequence that is partially homologous by having up to 30% base mismatches with the first DNA sequence and in which an enzymatic mismatch repair system is defective; mixing the two sets of cells to form diploids, maintaining the mixture under conditions to effect meiosis, and recovering cells of a hybrid eukaryotic species.

Although the method is applicable in principle to eukaryotes generally, it is expected to be of particular interest in relation to plants and unicellular organisms, such as protozoa, fungi, and particularly yeasts.

The invention provides a quick and convenient way of making hybrid eukaryotic species. By suitable marking and selection, it should be possible to make hybrids having improved characteristics, e.g. the desired characteristics of both parents. For example, current brewing yeasts are difficult to work with, and the process of the present invention may result in the production of hybrid strains that are easier to work with.

To test this proposal a hybrid of the bakers yeast to *S. cerevisiae* and its sibling species *Saccharomyces paradoxus* has been utilized. *S. paradoxus* (also described as *Saccharomyces douglasii*) is the closest relative of *S. cerevisiae* isolated to date. Electrophoretic karyotyping and hybridization analysis reveal that the genomes of the two species are very similar in terms of chromosome number, size and the location of genes. The weak hybridization of many cloned *S. cerevisiae* genes with *S. paradoxus* chromosomes demonstrates that DNA divergence exists between the two species. From the limited DNA sequence data available, divergence has been estimated to be ~11% and ~20% in coding and non-coding regions respectively. A hybrid of *S. cerevisiae* and *S. paradoxus* therefore comprises genome-wide homology but appears to lack major structural differences in karyotype.

The following experimental report examines meiotic recombination and chromosome disjunction in this hybrid and the effects of the mismatch repair genes PMS1 and MSH2 on these processes. However, this report and the experiments described therein should not be construed to limit the spirit and and scope of the claims.

Results

Experimental Rationale

The model depicted in FIG. 1 predicts that meiosis in nuclei containing divergent parental genomes will be associated with both low frequencies of reciprocal exchange and high frequencies of chromosome nondisjunction. This will lead to low viability of the meiotic products (reduced fertility). in the absence of mismatch recognition, crossovers will be permitted between homologous chromosomes, disjunction will be improved and a greater number of viable, euploid gametes will be produced.

The S. cerevisiae/S. paradoxus Hybrid

A wild-type, homothallic isolate of S. paradoxus, N17, has been engineered into a genetically tractable organism (see Materials and Methods). Hybrids of N17 and the S. cerevisiae strain Y55 produce only 1% viable spores (Table I and II, strain NHD47). Many of these have abnormal cell and colony morphologies and are slow growing, often producing only a microcolony. This sterility has been noted in similar hybrids and forms the basis of the biological species definition of yeast taxonomy.

The low spore viability of the hybrid is expected to be associated with high rates of chromosome nondisjunction. To test this prediction meiotic chromosome nondisjunction was monitored by physical analysis of the karyotypes of random spores. Separation of the yeast chromosomes by Clamped Homogenous Electric Field (CHEF) gel electrophoresis allows the assignment of disomy for the ten smallest Saccharomyces chromosomes. In the hybrid the frequency of disomy is high for all the chromosomes analyzed (Table III) with the exception of chromosome VI, which is always monosomic (see Discussion). Nondisjunction rates are up to 500-fold higher than that of a S. cerevisiae intraspecic diploid. The meiosis I nondisjunction rates of chromosomes IV and XI have been measured by a genetic analysis of random spores in a S. cerevisiae Y55 strain at $1.4 \times 10^{-4}$ and $5.0 \times 10^{-4}$ per meiosis, respectively Chromosome II exhibited the highest rate of nondisjunction in the wild-type hybrid at $2.7 \times 10^{-1}$ per meiosis. The distribution of disomes closely fits that expected from an average nondisjunction rate of 12.2%, for the nine chromosomes examined (see Data Analysis). If this calculation is extended to all sixteen Saccharomyces chromosomes we expect 12.5% of spores to have no disomes, 27.7% to have one, 22.9% two and 36.9% to have three or more disomes.

The primary cause of chromosome nondisjunction is proposed to be low frequencies of genetic exchange. To ascertain recombination frequencies random spores were monitored for recombination in four genetic intervals: HIS4-LEU2 and LEU2-MAT on chromosome III, TRPI-ADE8 on IV and CYH2-MET13 on VII (Table IV). The frequency of recombination is 11.5 to 79-fold reduced relative to the intraspecific control S. cerevisiae diploids (NHD50, 53 and 94). The TRPI to ADE8 interval demonstrates a profound reduction in map distance. This large genetic interval is 270 cM in S. cerevisiae. In the hybrid the markers are tightly linked, with a map distance of approximately 2 cM.

Mismatch-Repair Deficient Hybrids

To examine the effect of the mismatch repair system on meiosis in S. cerevisiae/S. paradoxus hybrids, we disrupted the PMS1 and MSH2 genes in haploids of both species to produce the hybrid diploids NHD45 and NHD94.

Spore viability is significantly improved in the pms1 and msh2 hybrids by 6.1 and 8.7-fold respectively (Table II). Moreover, the accumulation of haplo-lethal mutations due to the mutator phenotypes of pms1 or msh2 produce ~21% spore death in intraspecific diploids (Table II strains Y55-518, Y55-512, NHPD1 and NHPD2). Therefore, correcting for the death induced by mutation, the viability of the hybrids can be estimated to be 7.4 and 11.5-fold greater than that of the wild-type hybrid. The difference between the viability of the psm1 and msh2 hybrids is also significant. Additionally, it was noted that viable spores from msh2 hybrids are less abnormal in colony morphology and are faster growing, forming fewer microcolonies. This may be a direct phenotypic manifestation of lower levels of aneuploidy.

Reduced Aneuploidy in Mismatch Repair Mutants

The improvement in spore viability in the mismatch repair deficient hybrids is concomitant with significant reductions in disomy. In both the mutant hybrids there is an improvement in the disjunction of all the chromosomes analyzed (Table III). In the psm1 hybrid the total frequency of disomes is reduced 1.8-fold over the wild type hybrid. The improvement in disjunction is even greater in the msh2 hybrid, with a further 1.8 fold reduction in total disomes. This indicates a significant disparity between the pms1 and msh2 mutants with respect to chromosome disjunction. In addition, the distribution of disomes between the three hybrid diploids is significantly different. In the wild-type hybrid only 32% of spores are not disomic for any of the nine chromosomes analyzed and nearly 12% contain three or more disomes By comparison, 70% of the spores from the msh2 hybrid have zero disomes and no spores contain more than two disomes.

Recombination is Increased in psm1 and msh2 Hybrids

Genetic analysis of random spores from the psm1 mutant hybrid reveals a 2.3 to 10-fold increase in recombinants for the four intervals monitored. As might be expected from the disjunction data, the effect of the msh2 disruption is greater, producing a 6.0 to 16.5-fold increase in recombinant frequency. Again this reflects a significant difference between the two mutant hybrids. No change in recombinant frequency is observed in the psm1 and msh2, intraspecifc S. cerevisiae diploids (NHD53 and NHD95), demonstrating that the observed effects are specific to the hybrids. The improved spore viability of the msh2 hybrid permitted limited "tetrad analysis" to be performed. Out of 53 tetrads with one or more viable spores, 3.9% have a recombination event in the interval HIS4-LEU2, 19.6% between LEU2-MAT, 41.2% in TRPI-ADE9 and 3.8% between CYH2-MET13. These frequencies are not statistically different to those obtained from the analysis of random spores. In addition, bona fide reciprocal events in three of the four intervals analyzed (LEU2-MAT, TRPI-ADE8 and CYH2-MET13) were represented in the tetrads with two or more viable spores.

Meiotic crossing over is reduced between homeologous chromosomes.

Meiotic recombination in the partial hybrid can be monitored in four genetic intervals, covering approximately 250 kb of the 320-kb chromosome III. The frequency of exchange between the divergent chromosomes was determined by tetrad analysis. Recombination data were calculated from tetrads with four viable spores and from asci which yielded only three viable spores. For this latter class of tetrad, it is possible to predict the genotype of the dead spore from the segregation pattern of genetic markers observed in the remaining viable spores. Data from these two classes of tetrad are presented in Table V, and map distances are shown in Table VI. Recombination data for homologous mismatch repair-deficient strains were not determined, because previous control experiments have demonstrated that psm1 and msh2 mutants do not affect the rates of intergenic, meiotic recombination in a perfectly homologous diploid. Crossing over in the partial hybrid is suppressed in each of the four genetic intervals monitored. The HML-to-HIS4 map distance is contracted 60-fold when compared with that of the control Y55 homozygous diploids.

A 47-fold reduction in exchange is observed in the MAT-THR4 interval. Only one event is observed in the HIS4-LEU2 region in the 440 tetrads analysed. The smallest reduction is in the LEU2-MAT interval, which exhibits a nine-fold reduction in exchange. The average reduction over the entire interval from HML to THR4 is 25-fold. The overall reduction is even more extreme, 40-fold, if we consider only the four-viable-spore tetrad class (Table V).

Mismatch repair mutant partial hybrids are predicted to show elevated frequencies of recombination. A partial-hybrid diploid, homozygous for a deletion of the psm1 gene was constructed and tetrads were analysed (Tables V and VI). Reciprocal exchange is increased in three of the four intervals monitored; over the combined HML-to-THR4 region, there is a 2.5-fold increase over that in the wild-type partial hybrid. However, no stimulation of recombination is observed in the MAT-THR4 region. Overall, the HML-to-7HR4 map distance remains more than 10-fold reduced relative to the homologous controls. An msh2 partial hybrid was also constructed (Tables V and VI). Recombination in this strain is affected to a greater extent than in the pms1 diploid. The map distance is expanded 5.5-fold in the HML-THR4 interval relative to that in the wild-type partial hybrid. This represents a 4.5-fold reduction in recombination relative to the homologous controls. The frequency of exchange observed in the msh2 mutant is significantly greater than in the psm1 partial hybrid. Genetic exchange in a psm1 msh2 double mutant (Tables V and VI) increases significantly compared with that in the psm1 and msh2 partial hybrids (P<0.001 and P<0.01, respectively) over the whole HML-THR4 interval. The map distance increases by 7-fold in the double mutant relative to the wild-type partial hybrid and is only 3.5-fold reduced from the homologous control. The increase in map distance in the double mutant is the sum of the increases in the single mutants. The map distance of HML-THR4 is 34.7 centimorgans (cM) in the double mutant compared with 11.8 and 26.6 cM in the pms1 and msh2 single mutants respectively. These properties of the double mutant, compared to the single mutants, are completely unexpected.

The Meiotic Behavior of an Interspecific Yeast Hybrid Satisfies the Predictions of the Antirecombination Model The frequency of meiotic recombinants are reduced to between 1.3% and 8.7% of intraspecies frequencies over four genetic intervals that vary from 11 to 270 cM. The reduction is greatest over the largest region, TRF1 to ADE8. The map distance is reduced ~136-fold, predicting that a crossover in this interval will occur in less than 4% of meioses. The low recombination rates confer a several hundred-fold increase in the frequency of nondisjunction. However, we would have expected such low frequencies of recombination to be associated with an greater nondisjunction rate. For example, a 20-fold reduction in map distance for a 200 cM chromosome will result in a frequency of homologue pairs without reciprocal exchange ($E_o$) of 82% (see Data Analysis). If $E_o$ homologous then segregate randomly at meiosis I, 41% will nondisjoin. Such a high frequency of disomy is not seen for any of the chromosomes analyzed, although greater than 20-fold reductions in recombination do occur There are a number of explanations which could account for this observation. Firstly, the viable random spores may be underrepresented for aneuploidy because particular combinations of disomes are either lethal or produce slow growing colonies. In this study chromosome VI was never found to be disomic in over three hundred CHEF karyotypes. This could be because VI disomy is lethal. While this is not the case for intraspecific S. cerevisiae cells, in which VI disomy is tolerated, it is possible the S. cerevisiae and S. paradoxus chromosomes could be incompatible. Alternatively, it is possible that chromosome VI always disjoins correctly. The existence of a distributive pairing mechanism may also account for lower than expected levels of aneuploidy. Distributive pairing improves the segregation of $E_o$ and heterologous chromosomes, For example, a pair of heterologous yeast artificial chromosomes (YACs) do not recombine at detectable frequencies but only missegregate in 25% of meioses, not the expected 50%. Finally, the divergence between the two yeast species may be mosaic in nature. The degree of identity along the chromosomes and between different chromosomes may vary widely. Regions of high homology, that frequently recombine to ensure disjunction, could be present.

The Mismatch Repair Proteins PMS1 and MSH2 Reduce Meiotic Homologous Recombination The psm1 mutation restores meiotic recombination in the hybrid to between 9% and 27% of intraspecies frequencies. In msh2 hybrids the frequency of recombinants is 20% to 69% of the homologous controls. The increase in TRP1-ADE8 map distance in the msh2 hybrid predicts a crossover will occur in nearly 50% of meioses. However, this is still a low frequency when compared to the intraspecies S. cerevisiae interval which has approximately 5 crossovers per meiosis. Recombinants are observed in spores from tetrad dissection at frequencies equivalent to those from random spore analysis. It is important to note that both products of reciprocal exchange events are recovered in the tetrads with two or more viable spores from this analysis. This indicates that random spore recombinants represent true crossover products. The psm1 and msh2 Y55 intraspecific, control diploids have no increase in the frequency of meiotic recombination. These controls rule out the possibility that the increase in recombinants in the mutant hybrids is due to a general hyperrecombination phenotype or to marker reversion. We conclude that the mismatch repair system actively inhibits meiotic exchange between highly divergent chromosomes.

The observation that recombination is never fully restored in mismatch repair deficient hybrids could be due to several factors Other mismatch repair proteins, that inhibit homologous recombination, may still be active in these mutants. Also, the degree of initiation of meiotic recombination may be reduced between homologous chromosomes. This "trans effect" of heterozygosity has been observed at two loci in S. cerevisiae. Also some regions of the chromosomes may be so diverged that homology is no longer recognized at the strand exchange stage of recombination (see also below).

To determine if PMS1 and MSH2 are operating in the same or different pathways during homeologous exchanges, a psm1 msh2 double-mutant strain was constructed. Because Pms1p and Msh2p are proposed to act in concert, we would have predicted that a double mutant would be no more severe than either mutant alone. Analysis of post-meiotic segregation frequencies and rates of mitotic mutation support this proposal. However, with respect to meiotic homeologous recombination, the phenotype of the double mutant is more severe. The total increase in homeologous recombination in the double mutant significantly exceeds the rates of exchange observed in either the psm1 or msh2 strain (P<0.001 and P<0.01, respectively). In fact, the rates of exchange in the double mutant are additive.

Crossovers Ensure Disjunction

The correlation between greater crossing over and decreased aneuploidy indicates that many of the crossovers restored in the mutant hybrids can ensure disjunction, that is, can form functional chiasmata (a cytological manifestation of crossing over). This relationship between crossover frequency and chromosome disjunction is not linear. From a comparison with S. cerevisiae recombination mutants we propose that the deficiency of recombination is the major reason for nondisjunction in the hybrid. For example, the med1 mutation, an allele of the DMCl gene, has a 2-fold decrease in meiotic crossovers, 4.3% chromosome III and 6.6% chromosome VIII disomes, and 20% spore viability. This is similar to the msh2 hybrid which has approximately a 3-fold decrease in exchange, 6% chromosome III and 3% chromosome VIII disomes, and 10% spore viability.

It must also be considered that the reduced fidelity of recombination in mismatch repair deficient hybrids may increase the frequency of crossovers between related, ectopic loci. Ectopic crossovers are known to interfere with homologue disjunction and are likely to produce lethal, unbalanced translocations. One such translocation, giving rise to a unique sized chromosomal species has been observed in a segregant from the msh2 hybrid (not shown).

Spore Viability is Improved in psm1 and msh2 Hybrids

The increased spore viability appears to be a direct consequence of improved chromosome disjunction which in turn is the result of increased frequencies of meiotic recombination. The spore viability of the hybrids are lower than expected from the patterns of disomy observed. The average frequency of disomes in random spores from the msh2 hybrid is 3.7% per chromosome. The observed frequency of 70% spores with no disomes, for the nine chromosomes examined, closely fits the expected frequency. If this rate of disomy is assumed for all sixteen *Saccharomyces* chromosomes, the expected number of spores with no disomes is 55%. Therefore the minimum expected spore viability for the msh2 hybrid is 55%. The fact that spore viability is not restored to this level indicates that other factors probably contribute to the meiotic sterility of the *S. cerevisiae/S. paradoxus* hybrid. The observation that some *S. paradoxus* chromosomes are haplo-insufficient in an otherwise *S. cerevisiae* genetic background, suggests that chromosomal rearrangements or incompatibilities, that could contribute significantly to spore inviability, may be present between the two species.

In summary, an active mismatch repair system reduces meiotic exchange between divergent chromosomes, increases their rate of nondisjunction and reduces spore viability.

Processing of Mismatched Recombination Intermediates

How the mismatch repair system processes mismatched recombination intermediates at the molecular level is not clear. Several models have been proposed. The "killer mechanism" causes the destruction of intermediates which could potentially lead to chromosomal loss. Mismatch repair-induced recombination may lead to chromosomal rearrangement or loss. Lastly, antirecombination and the similar "heteroduplex rejection" models propose that intermediates are aborted via disassembly, or resolution without exchange. From the data presented here none of these possibilities can be excluded. However, the low frequencies of meiotic exchange and high levels of aneuploidy are most consistent with an antirecombination mechanism.

Several observations, from a variety of experimental approaches, suggest that recombination intermediates are disrupted at an early stage, prior to the formation of a stable heteroduplex junction. Firstly, individual components of the bacterial mismatch repair system can block in vitro homologous strand exchange catalyzed by the *E. coli* RecA protein. Also recombination intermediates that have been detected during meiotic prophase 1, in *S. cerevisiae*, were not observed to form between homologous chromosomes. Finally, F1 hybrids between species of Allium that lack gross chromosomal rearrangements have a substantial reduction in the frequency of chiasma and an increased number of univalents at pachytene.

Mutations in the mismatch repair genes MSH2 and MSH3 have been shown to increase the frequency of mitotic homologous recombination, in *S. cerevisiae,* between substrates with 73% identity. Mutation of PMS1 had no significant effect on recombination, an observation made by other workers utilizing mitotic recombination assays with similarly diverged substrate DNA (~80% identity). However in a recent mitotic study, a 10-fold effect of psm1 was observed with 92% identical substrates. In the data presented here, psm1 produces up to a 10-fold enrichment in meiotic recombinants. The effect of msh2 is significantly greater, not only in terms of recombination, but also for disomy and spore viability. This observation suggests that the method of processing recombination intermediates depends upon the degree of divergence between the participating molecules. At relatively high levels of divergence (10–30%) MSH2 appears to have a greater role than PMS1 in preventing homologous recombination.

From the known biochemical properties of the *E. coli* MutS and *S. cerevisiae* MSH2 proteins it is assumed that DNA divergence will be recognized when mismatches form in heteroduplex DNA. A number of features of meiotic homologous recombination follow from this assumption The fact that reasonable frequencies of recombination are observed in pms1 and msh2 hybrids suggests that the induction of meiotic recombination is still high Also, consistent with the in vitro properties of *E. coli* RecA protein, high densities of mismatches are not normally inhibitory to strand exchange per se in yeast. However, very high divergence (greater than 30% mismatches) may act as a structural barrier to strand exchange.

Materials and Methods

Strains

All *S. cerevisiae* and *S. paradoxus* strains used in this study are isogenic derivatives of Y55 and N17 respectively Genotypes are described in Table I. The ho-ochre mutation was isolated by UV-mutagenesis but was found to have a slightly leaky phenotype.

Subsequently, heterothallic strains were obtained by creating a 100 bp PstI deletion of the coding sequence of the HO gene. The Δpsm1 mutation is a 2.6 kb deletion of the PMS1 coding sequence. Both hoΔPst and Δpms1 were cloned into a URA3 selectable, integrative vector and introduced via two-step gene replacement. The pms1 Δ::URA3 mutation is a URA3 replacement of 2.6 kb of the PMS1 coding sequence. msh2:: LEU2 is an insertion of LEU2 at a Sna BI site of the wild-type gene in plasmid pII-2, Both were introduced by one-step gene transplacement. his4-RI, trpl-bsu36 and ura3-nco are restriction site fill-in mutations leu2 Δ is a deletion of most of the LEU2 coding region. All were introduced by two-step gene replacement. Other auxotrophic markers were spontaneous or UV-induced. All transformations were verified by Southern blot analysis using the digoxigenin, nonradioactive system as recommended by the manufacture (Boehringer Mannheim).

A psm1 msh2 double mutant was created by two-step gene replacement with the BstXI fragment of pWK4Δpsm1 followed by one-step gene transplacement of the SpeI fragment of pII-2–7.

The resulting strain had this genotype.

```
MATa HML::ADE1 his4-r leu2-r thr4-a^b   KAR1
MATα  HML     HIS4   LEU2   THR4^c      kar1-Δ13 ade1-1 can1-1 ura3-n pms1Δ msh2::URA3 CYH2   lys2-d
ade1-1 CAN1   ura3-n pms1Δ msh2s::URA3 cyh2-1 LYS2
```

Genetic Procedures

Yeast manipulations and media were as described in the literature. Strains were grown on YPD and synthetic complete media lacking one or more amino acids, at 30° C. Sporulation was performed at room temperature on KAc plates: 2% potassium acetate, 0.22% yeast extract, 0.05% glucose, 2.5% agar 0.09% complete amino-acid mixture. Dissected tetrads were grown for 3–7 days at 30° C. Germination was scored microscopically after 3 days. Only spores that formed microcolonies were scored as being viable. Random spores were prepared and grown on synthetic complete media lacking arginine, containing cycloheximide (10 mg/L) and canavanine (40 mg/L) for 3–6 days at 30° C. One and two-step gene replacement was performed. Yeast transformation was carried out using a modification of the lithium acetate method.

Chromosome Transfer by Karl

Strains that were partially hybrid for chromosome III were created by karl-mediated single-chromosome transfer from N17 into Y55-2395 by a modification of previously described methods. Chromosome transfer events were selected on synthetic medium lacking leucine and supplemented with cycloheximide (10 mg/liter). Strains disomic for chromosome III, which arise from the chromosome transfer event, were confirmed physically by the appearance of a band of double intensity by CHEF gel analysis and genetically by a nonmating sporulation-deficient phenotype.

Selection for Loss of the Resident Y55 Chromosome III

S. cerevisiae strains monosomic for the N17 chromosome III were constructed by transplacing the EcoRI fragment of pGEM7.10ΔCXURA3 (a URA3 disruption of the MSH3 open reading frame) into the disomic strains obtained from chromosome transfer. Transplacement occurs preferentially into the Y55 copy of the MSH3 gene because of reduced homology with the S. paradoxus chromosome. Subsequently, 5-fluoroorotic acid selection for ura3' strains was used to obtain haploids which had lost the resident Y55 chromosome. The resulting monosomic strains are α maters with the S. paradoxus III genotype.

Karyotyping of Segregants

Random spore segregants were karyotyped. Disomy was assigned via band intensity or the presence of two bands for co-migrating and polymorphic chromosomes respectively.

Data Analysis

Data sets were analyzed using the standard normal, nonparametric sign and G-tests. The G-test is an equivalent to the $X^2$ contingency test. Values of $P<0.05$ were considered significant. Expected distributions of disomes were calculated using the average disomy frequencies in a binomial expansion involving 9 or 16 chromosomes, $E_o$ values were calculated assuming recombination rates in random spores are equivalent to map distance and a poisson distribution of the number of crossovers per chromosome.

TABLE I

Strains used in this study

| Strain | Genotype | Reference |
|---|---|---|
| Y55 | S.c. HO wild type | (McCusker, 1988) |
| N17 | S.p. HO wild type | (Naumov, 1990) |
| Y55-518 | S.c. hoΔPst MATα arg4-1 HIS6 leu2-1 trp5-1 μra3-nco Δpms1 | This study |
| | S.c. hoΔPst MATα arg4-1 his6-1 leu2-1 TRP5 μra3-1 Δpms1 | |
| Y55-512 | S.c. ho-ochre MATα arg4-1 HIS6 leu2-1 trp5-1 μra3-1 msh2::LEU2 | This study |
| | S.c. ho-ochre MATα arg4-1 his6-1 leu2-1 TRP5 μra3-1 msh2::LEU2 | |
| NHPD1 | S.p. hoΔPst MATα CAN1 cyh2-1 lys2-1 LYS5 μra3-1 pms1Δ::URA3 | This study |
| | S.p. hoΔPst MATα can1-1 CYH2 LYS2 lys5-1 μra3-1 pms1Δ::URA3 | |
| NHPD2 | S.p. hoΔPst MATα CAN1 cyh2-1 lys2-1 LYSS μra3-1 msh2:URA3 | This study |
| | S.p. hoΔPst MATα can1-1 CYH2 LYS2 lys5-1 μra3-1 msh2:URA3 | |
| NHD50 | S.c. hoΔPst MATα ade8-1 can1 CYH2 his4-R1 Leu2Δ met13-4 trp1-bsu36 μra3-nco | This study |
| | S.c. hoΔPst MATα ADE8 CAN1 cyh2-1 HIS4 LEU2 MET13 TRP1 μra3-nco | |
| NHD53 | S.c. hoΔPst MATα ade8-1 can1 CYH2 his4-R1 leu2Δ met13-4 trp1-bsu36 μra3-nco pms1Δ::URA3 | This study |
| | S.c. hoΔPst MATα ADE8 CAN1 cyh2-1 HIS4 LEU2 MET13 TRP1 μra3-1 pms1Δ::URA3 | |
| NHD95 | S.c. hoΔPst MATα ade8-1 can1 CYH2 his4-R1 leu2Δ met13-4 trp1-bsu36μra3:nco msh2-URA3 | This study |
| | S.c. hoΔPst MATα ADE8 CAN1 cyh2-1 HIS4 LEU2 MET13 TRP1 μra3-1 msh2:URA3 | |
| NHD47 | S.c. hoΔPst MATα ade8-1 can1 CYH2 his4-R1 leu2Δ met13-4 trp1-bsu36 μra3-nco | This study |
| | S.p. hoΔPst MATα ADE8 CAN1 cyh2-1 HIS4 LEU2 MET13 TRP1 μra3-1 | |

TABLE I-continued

Strains used in this study

| Strain | Genotype | Reference |
|---|---|---|
| NHD45 | S.c. hoΔPst MATα ade8-1 can1 CYH2 his4-R1 leu2Δ met13-4 trp1-bsu36 μra3-nco pms1Δ::URA3<br>S.p. hoΔPst MATα ADE8 CAN1 cyh2-1 HIS4 LEU2 MET13 TRP1 μra3-1 pms1Δ::URA3 | This study |
| NHD94 | S.c. hoΔPst MATα ade8-1 can1 CYH2 his4-R1 leu2Δ met13-4 trp1-bsu36 μra3-nco msh2:URA3<br>S.p. hoΔPst MATα ADE8 CAN1 cyh2-1 HIS4 LEU2 MET13 TRP1 μra3-1 msh2:URA3 | This study |

Abbreviations: S.c., *Saccharomyces cerevisiae*: S.p., *Saccharomyces paradoxus*. All S.c. and S.p. strainsare isogenic to the wild-type isolates Y55 and N17 resectively. Strains were constructed as described in Methods and Materials.

TABLE II

Spore viabilities of intraspecific and hybrid yeast diploids

| Stain | Genotype | Percentage spore Viability |
|---|---|---|
| Y55 | S.c. wt | 97.8 (841/860) |
| N17 | S.p. wt | 97.0 (194/200) |
| Y55-518 | S.c. pms1 | 80.5 (679/844) |
| NHPD1 | S.p. pms1 | 71.3 (117/164) |
| Y55-512 | S.c. msh2 | 84.0 (776/924) |
| NHPD2 | S.p. msh2 | 80.42 (193/240) |
| NHD47 | Hybrid wt | 1.2 (10/852) |
| NHD45 | Hybrid pms1 | 7.2 (63/880) |
| NHD94 | Hybrid msh2 | 10.2 (147/1440) |

Diploids were sporulated and tetrad ascospores dissected. To reduce the spore death caused by the mutator phenotypes of pms1 and msh2, vegetative growth as a diploid was minimised. Haploid strains were mated for only 6 hrs at 30° C., and the diploids were not selected prior to sporulaton. All strains were treated in this way. The spore viability of all three hybrids is significantly different from all intraspecific diploids as determined by standard normal test (P<0.001). The pms1 and msh2 hybrid viabilities are different from the wild-type hybrid (P<0.01 and P<<0.001 respectively), and the msh2 hybrid is different from the pms1 hybrid (P<0.01).

TABLE III

Frequency of disomes in hybrid segregants
Percentage of Spores With Disome

| Strain | I | VI | III | IX | VIII | XI | X | XIV | 11 | Total |
|---|---|---|---|---|---|---|---|---|---|---|
| NHD47 (wi) | 18.4 (19/103) | 0.0 | 9.7 (10/103) | 12.6 (13/103) | 21.4 (22/103) | 5.8 (6/103) | 13.6 (14/103) | 1.0 (1/103) | 27.2 (28/103) | 12.2 (113/927) |
| NHD45 (pmsl) | 13.3 (14/105) | 0.0 | 7.6 (8/103) | 5.7 (6/105) | 7.6 (8/105) | 1.9 (2/105) | 8.6 (9/105) | 0.0 | 14.3 (15/103) | 6.6 (62/945) |
| NHD94 (msh2) | 4.0 (4/100) | 0.0 | 6.0 (6/100) | 4.0 (4/100) | 3.0 (3/100) | 5.0 (5/100) | 7.0 (5/100) | 0.0 | 4.0 (4/100) | 3.7 (33/900) |

Random segregants were karyotyped by CHEF gel electrophoresis. The total numbers of disomes are significantly different between all three data sets as defined by a standard normal test (P < 0.01 to P << 0.001) and the individual data sets are different by non-parametric sign test (P < 0.05 to P < 0.01). The data sets for chromosomes VIII and II are different between NHD47 and NHD45(P < 0.01 and P < 0.05 respectively). Chromsome I, IX, VII, X, and II data sets are different between NHD47 and NHD94 (P < 0.05 to P <<0.001). The frequency of disomes for chromsomes I and II are significantly different between NHD45 and NHD94 (P < 0.01).

TABLE IV

Meioitic recombination

Percentage Recombinants

| Strain | HIS4-LEU2 | LEU2-MAT | TRP1-ADE8 | CYH2-MET13 |
|---|---|---|---|---|
| NHD50 (S.c. wt) | 18.33 (66/360) | 21.67 (78/360) | 46.39 (167/400) | 11.94 (43/360) |
| NHD53 (S.c. pms1) | 17.22 (62/360) | 24.72 (89/360) | 49.44 (178/360) | 11.94 (43/360) |
| NHD95 (S.c. msh2) | 23.8 (86/360) | 22.78 (82/360) | 47.5 (171/360) | 9.17 (33/360) |
| NHD47 (Hybrid wt) | 0.25 (1/400) | 2 (8/400) | 2 (8/400) | 0.25 (1/400) |
| NHD45 (Hybrid pms1) | 1.75 (7/400) | 4.5 (18/400) | 13 (52/400) | 2.5 (10/400) |
| NHD94 (Hybrid msh2) | 4 (16/400) | 12 (48/400) | 33 (132/400) | 3.5 (14/400) |

Random spores were analysed for recombination in the four intervals shown. Map distance is equivalentto the frequency of recombinants. None of the intervals in the control diploids, NHD50, 53 and 95 are statistically-different by standard normal test. Therefore a pool of these data sets was used for comparison to data for thehybrid diploids. All intervals in the three hybrid diploids are significantly different to intraspecific controls($P \ll 0.001$). The recombinant frequency in all four intervals in the pms1 hybrid is statistically differentto the wild-type hybrid ($P < 0.05$ to $P \ll 0.001$). Likewise all intervals are different between msh2 andwild-type hybrids ($P < 0.001$ to $P \ll 0.001$). Additionally, the LEU2-MAT and TRP1-ADE8 data sets aredifferent between pms1 and msh2 hybrids ($P \ll 0.001$) and the HIS4-LEU2 data is suggestive of a difference($P = 0.056$). The total number of recombinants is also significantly different between the three hybrids ($P \ll 0.001$).

TABLE V

Total meiotic recombination in tetrads with three and four viable spores

% Recombination in tetrad class[a]
Total recombination %

| Strain | 4 spores | 3 spores |
|---|---|---|
| Wild-type homozygote | 200[b] (665/333) | 185[b] (24/13) |
| Wild-type partial hybrid | 5.04 (18/357) | 28.9 (24/83) |
| pms1 partial hybrid | 22.1 (31/140) | 26.3 (20/76) |
| msh2 partial hybrid | 47.4 (65/137) | 66.1 (39/59) |
| pms1 msh2 partial hybrid | 63.2 (72/114) | 78.0 (64/82) |

[a]Recombination data are pooled from two independent diploids for each cross. Numbers in parenthesesrepresent total numbers of reciprocal exchange events including twice the number of nonparental ditypes (non-parentaldiploids were observed only in the wild-type homologous diploids
[b]Each tetrad in the wild-type homologous control had more than one crossover across the whole intervalmonitored, hence the >100% total recombination observed.

TABLE VI

Genetic Map Distances

| Strain | Map distance (cM) of genetic interval[a] Total HML-THR4 | Fold Reduction |
|---|---|---|
| Wild-type homozygous control | 120 | 1.0 |
| Wild-type partial hybrid | 4.8 | 25.0 |
| pms1 partial hybrid | 11.8[b] | 10.2 |
| msh2 partial hybrid | 26.6[b] | 4.51 |
| pms1 msh2 partial hybrid | 34.7[b] | 3.46 |

[a]Map distance in centimorgans (cM) is calculated as described in Materials and Methods.
[b]Values significantly deviating from those for the wild-type partial hybrid ($P < 0.001$).

The invention claimed is:

1. A process for making hybrid yeast cells with recombined DNA sequences comprising:
    (a) mutating a first set of haploid yeast cells to render defective the enzymatic mismatch repair system of the first set of cells and introducing a first DNA sequence into the first set of cells;
    (b) mutating a second set of haploid yeast cells to render defective the enzymatic mismatch repair system of the second set of cells and introducing a second DNA sequence into the second set of cells wherein the second DNA sequence is partially homologous to the first DNA sequence and has up to 30% base mismatches with the first DNA sequence;
    (c) mixing the first and second sets of cells to form diploid yeast cells;
    (d) culturing the diploid yeast cells to effect meiosis of the diploid yeast cells wherein said meiosis results in hybrid yeast cells comprising a recombination of the partially homologous first and second DNA sequences; and
    (e) recovering the hybrid yeast cells with recombined DNA sequences.

2. A process for obtaining recombined DNA sequences comprising:
    (a) conducting the process according to claim 1 to make hybrid yeast cells; and
    (b) isolating recombined DNA sequences of the hybrid yeast cells.

3. The process according to claim 2, wherein the recombined DNA sequences comprise a gene.

4. A process for obtaining proteins encoded by recombined DNA sequences comprising:
    (a) obtaining the recombined DNA sequences according to the process of claim 2; and
    (b) expressing proteins encoded by the recombined DNA sequences.

5. The process according to claim 4, wherein the recombined DNA sequences comprise a gene.

* * * * *